US00PP09369P

United States Patent [19]

VandenBerg

[11] Patent Number: Plant 9,369

[45] Date of Patent: Nov. 14, 1995

[54] CHRYSANTHEMUM PLANT NAMED 'SANDUSKY'

[75] Inventor: Cornelis P. VandenBerg, Salinas, Calif.

[73] Assignee: Yoder Brothers, Inc., Barberton, Ohio

[21] Appl. No.: 331,857

[22] Filed: Nov. 1, 1994

[51] Int. Cl.[6] ..... A01H 5/00

[52] U.S. Cl. ..... Plt./82.2

[58] Field of Search ..... Plt./82.2

*Primary Examiner*—Howard J. Locker

*Attorney, Agent, or Firm*—Foley & Lardner

[57] ABSTRACT

A Chrysanthemum plant named Sandusky particularly characterized by its flat capitulum form; daisy capitulum type; yellow ray floret color; diameter across face of capitulum of 70 to 79 mm when fully opened, when grown as a pinched spray pot mum; photoperiodic flowering response to short days of 50 to 56 days; plant height with 14 long days after sticking unrooted cuttings, and with 0 to 1 applications of 2500 ppm B-9 SP, ranges from 23 to 30 cm when grown as a pinched pot mum with four (4) cuttings in a 15 cm pot; branching pattern is spreading and prolific, each plant having 4 to 6 laterals after pinch; and recommended as a spray pot mum.

3 Drawing Sheets

The present invention comprises a new and distinct cultivar of Chrysanthemum, botanically known as *Dendranthema grandiflora,* and referred to by the cultivar name Sandusky.

Sandusky, identified as 6281 (90-184004), was originated from a cross made by Cornelis P. VandenBerg in a controlled breeding program in Salinas, Calif., in 1989.

The female parent of Sandusky was an unnamed seedling identified as 4170 (86-469002) and described as a pot spray mum with flat capitulum form; daisy capitulum type; yellow ray floret color; diameter across face of capitulum of 57 to 70 mm when grown as a spray pot mum; flowering response to short days in Salinas, Calif. of 50 to 59 days; plant height of 23 to 33 cm when grown with 15 to 16 long days after sticking unrooted cuttings prior to start of short days and one (1) application of 2500 ppm B-9 SP; and a branching pattern of 3 to 5 laterals developing after pinch. The female parent was discarded from all programs on Dec. 7, 1989.

The male parent of Sandusky was an unnamed seedling identified as 1777 (83-811010), and described as a pot spray mum with flat capitulum form; daisy capitulum type; white ray floret color; diameter across face of capitulum of 70 to 76 mm when grown as a spray pot mum; flowering response to short days in Salinas, Calif. of 53 to 62 days; plant height of 20 to 30 cm when grown with 15 to 16 long days after sticking unrooted cuttings prior to start of short days and 2 to 3 applications of 2500 ppm B-9 SP; and a branching pattern of 3 to 4 laterals developing after pinch. The male parent was discarded from all programs on Oct. 30, 1990.

Sandusky was discovered and selected as one flowering plant within the progeny of the stated cross by Cornelis P. VandenBerg in May 1991, in a controlled environment in Salinas, Calif.

The first act of asexual reproduction of Sandusky was accomplished when vegetative cuttings were taken from the initial selection in July 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Sandusky are firmly fixed and are retained through successive generations of asexual reproduction.

Sandusky has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Sandusky, which, in combination, distinguish this Chrysanthemum as a new and distinct cultivar:

1. Flat capitulum form.
2. Daisy capitulum type.
3. Yellow ray floret color.
4. Diameter across face of capitulum of 70 to 79 mm when fully opened, when grown as a pinched spray pot mum.
5. Photoperiodic flowering response to short days of 50 to 56 days.
6. Plant height with 14 long days after sticking unrooted cuttings, and with 0 to 1 applications of 2500 ppm B-9 SP, ranges from 23 to 30 cm when grown as a pinched pot mum with four (4) cuttings in a 15 cm pot.
7. Branching pattern is spreading and prolific, each plant having 4 to 6 laterals after pinch.
8. Recommended as a spray pot mum.

The accompanying photographic drawings show typical inflorescence and leaf characteristics of Sandusky, with the colors being as nearly true as possible with illustrations of this type.

Sheet 1 is a color photograph of Sandusky grown as a pinched spray pot mum with four (4) cuttings in a 15 cm pot.

Sheet 2 is a black and white photograph of three views of the inflorescence of Sandusky.

Sheet 3 is a black and white photograph showing the upper and under sides of the leaves of Sandusky at three stages of development (mature, intermediate and immature). In sheets 2 and 3, a measuring tape in centimeters has been added.

Of the commercial cultivars known to the inventor, the most similar in comparison to Sandusky is the cultivar Yellow Dana, disclosed in U.S. Plant Pat. No. 8,330. Reference is made to attached Chart A, which compares certain characteristics of Sandusky to the same characteristics of Yellow Dana.

Similar traits are capitulum form and type, ray floret color, and recommendation as a spray pot mum. Sandusky has a smaller diameter of capitulum than Yellow Dana, and a faster flowering response to short days of 1 to 3 days. The plant height of both cultivars is comparable, although in several trials Sandusky exhibited a shorter plant height. In several trials, Sandusky also developed one more lateral after pinch than Yellow Dana.

In the following description color references are made to the Royal Horticultural Society Colour Chart. The color values were determined on plant material grown as a pinched spray pot mum in Salinas, Calif. on Apr. 29, 1994.

Classification:

*Botanical.*—*Dendranthema grandiflora* cv Sandusky.

*Commercial.*—Daisy spray pot mum.

INFLORESCENCE

A. Capitulum:

*Form.*—Flat.

*Type.*—Daisy.

*Diameter across face.*—70 to 79 mm when fully opened.

B. Corolla of ray florets: *Color* (*general tonality from a distance of three meters*).—Yellow. *Color* (*upper surface*).—5A. *Color* (*under surface*).—6B. *Shape.*—See photograph.

C. Corolla of disc florets:

*Color* (*mature*).—15A.

*Color* (*immature*).—144B.

D. Reproductive organs:

*Androecium.*—Present on disc florets only; no pollen.

*Gynoecium.*—Present on both ray and disc florets.

PLANT

A. General appearance:

*Height.*—23 to 30 cm when grown as a pinched pot mum with four (4) cuttings in a 15 cm pot with 14 long days after direct sticking unrooted cuttings prior to start of short days, and 0 to 1 applications of 2500 ppm B-9 SP.

*Branching pattern.*—Spreading and prolific, with 4 to 6 laterals after pinch.

B. Foliage:

*Color* (*upper surface*).—147A.

*Color* (*under surface*).147B.

*Shape.*—See photograph.

CHART A

COMPARISON OF SANDUSKY AND YELLOW DANA

| CHARACTERISTICS | SANDUSKY | YELLOW DANA |
|---|---|---|
| Ray floret color | Yellow | Yellow |
| Capitulum form and type | Flat daisy | Flat daisy |
| Diameter across face of capitulum | 70 to 79 mm | 76 to 80 mm |
| Flowering response | 50 to 56 days | 53 to 57 days |
| Plant height with 14 to 16 long days | 23 to 30 cm | 28 to 30 cm |
| Branching pattern | 4 to 6 laterals | 4 to 5 laterals |
| Recommended as | Spray pot mum | Spray pot mum |

COMPARISONS MADE OF PLANTS GROWN AS PINCHED SPRAY POT MUMS IN SALINAS, CALIFORNIA

I claim:

1. A new and distinct Chrysanthemum plant named Sandusky, as described and illustrated.

* * * * *

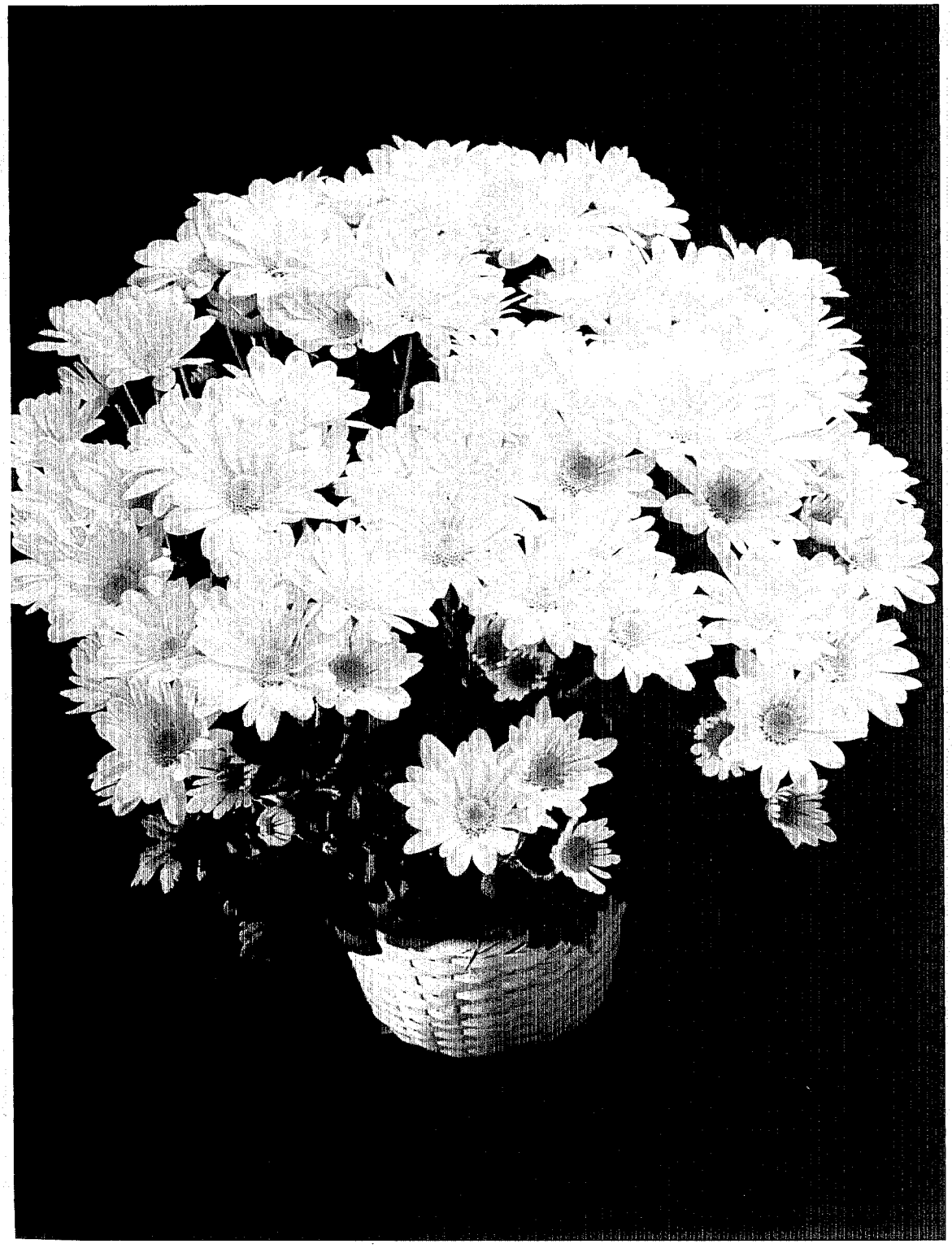

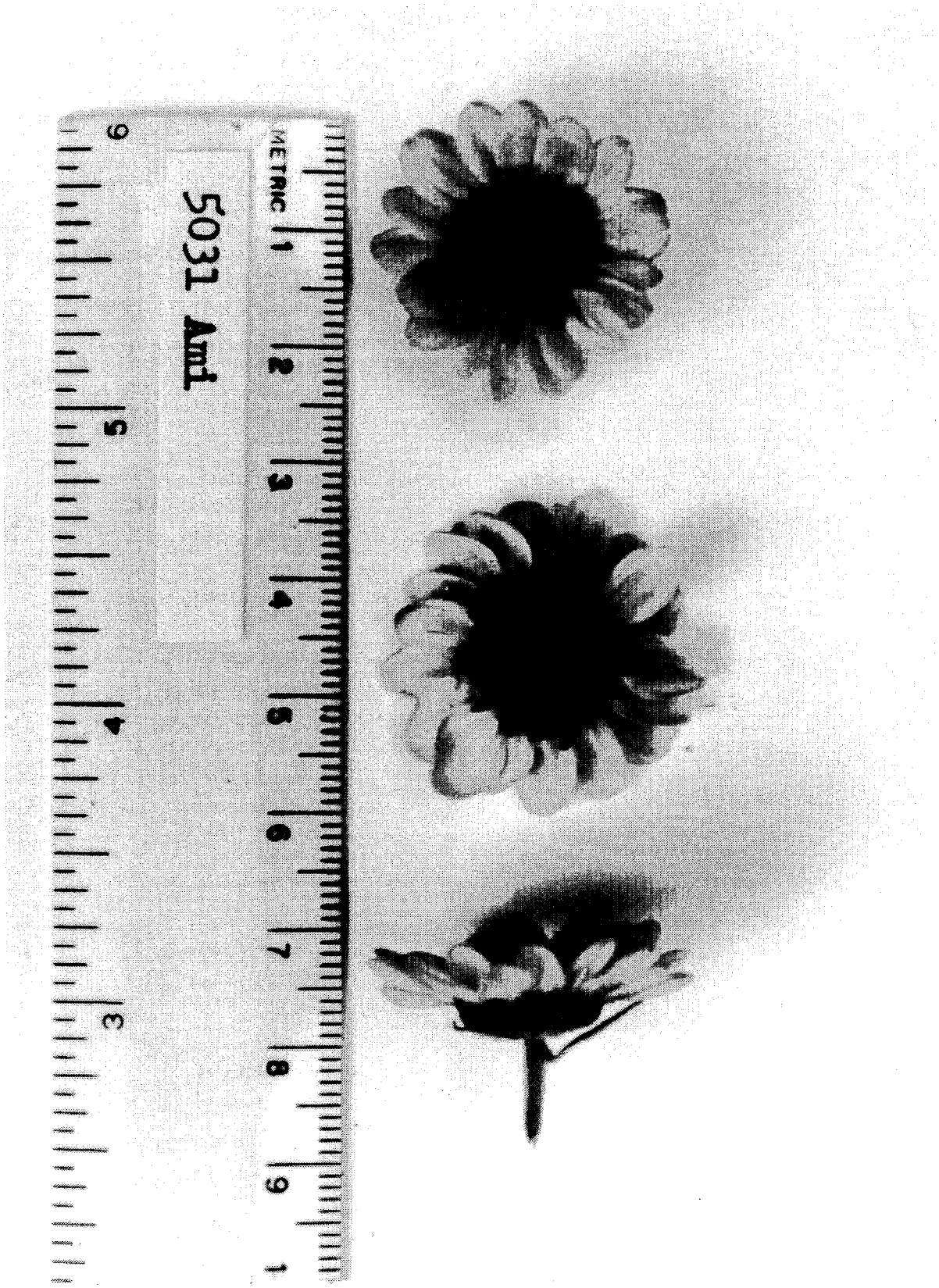
METRIC
5031 Amd

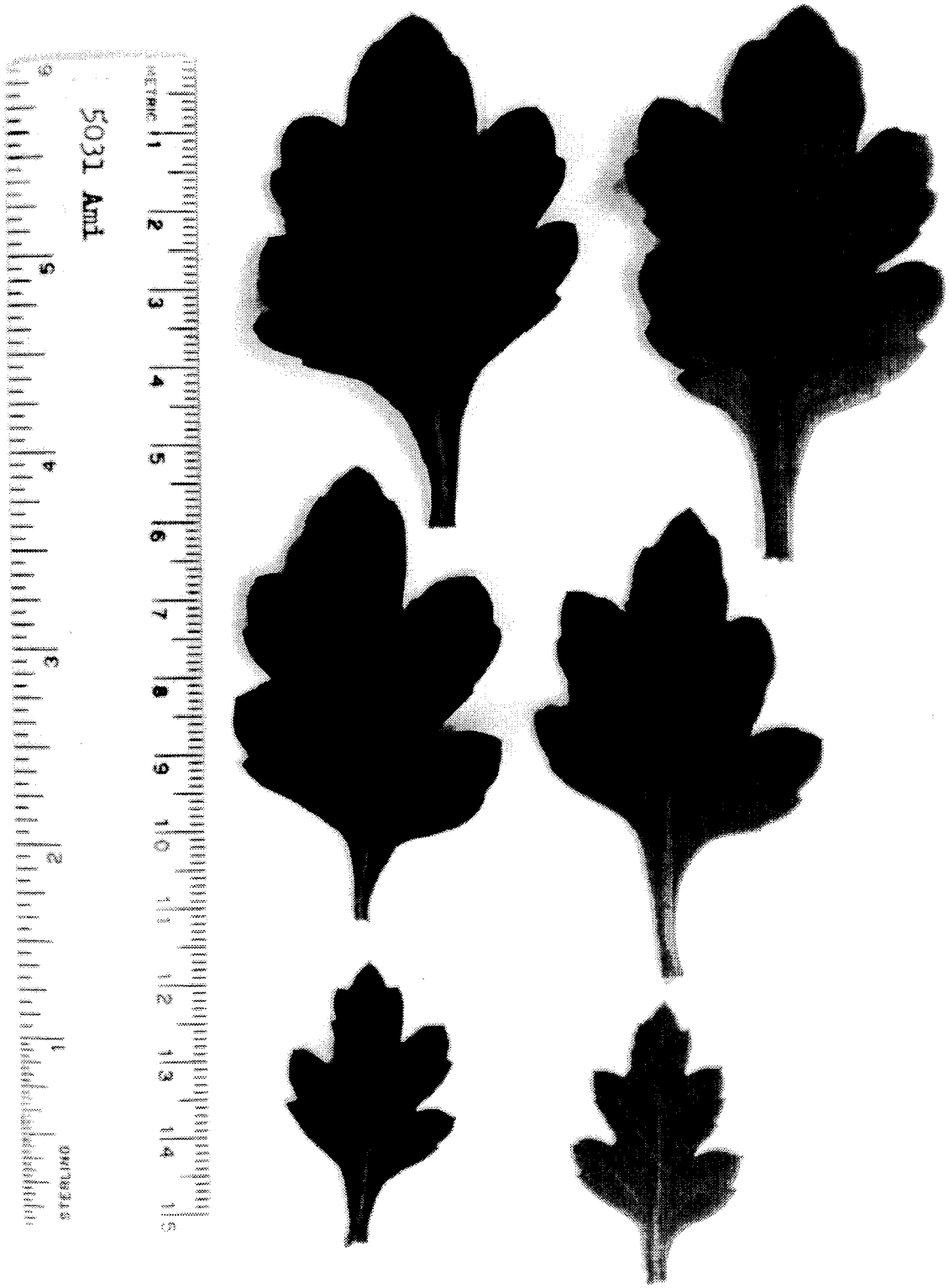
5031 Am1
STERLING